US010234467B2

(12) United States Patent
Merchant et al.

(10) Patent No.: US 10,234,467 B2
(45) Date of Patent: Mar. 19, 2019

(54) APPARATUS AND METHOD FOR TESTING MEDICAMENTS

(71) Applicant: UCL Business PLC, London, Greater London (GB)

(72) Inventors: Hamid Ali Merchant, London (GB); John Andrew Frost, London (GB); Abdul Waseh Basit, Harrow (GB)

(73) Assignee: UCL Business PLC, London. Greater London ( * ) Notice: Subject to any disclaimer, the term of this patent is extended or adjusted under 35 U.S.C. 154(b) by 94 days.

(21) Appl. No.: 15/392,113

(22) Filed: Dec. 28, 2016

(65) Prior Publication Data

US 2017/0108519 A1     Apr. 20, 2017

Related U.S. Application Data

(63) Continuation of application No. 14/398,385, filed as application No. PCT/GB2013/051145 on May 2, 2013, now abandoned.

(30) Foreign Application Priority Data

May 2, 2012   (GB) .................................. 1207677.4

(51) Int. Cl.
*G01N 31/00* (2006.01)
*G01N 31/16* (2006.01)
(Continued)

(52) U.S. Cl.
CPC ........... *G01N 33/84* (2013.01); *G01N 27/302* (2013.01); *G01N 33/15* (2013.01)

(58) Field of Classification Search
CPC .............................. G01N 31/16; G01N 31/00
(Continued)

(56) References Cited

U.S. PATENT DOCUMENTS 4,335,438 A    6/1982 Smolen 5,804,775 A    9/1998 Hu
(Continued)

FOREIGN PATENT DOCUMENTS

| EP | 1777510 | 4/2007 |
| JP | 11221433 | 8/1999 |
| WO | 2005116635 | 12/2005 |

OTHER PUBLICATIONS

Edwards et al. "A Comparison of the Suitabilites of rectal, gut and insulated axilla temperatures for measurement of the circadian rhythm of core temperature in field studies," Chronobiol Int. 19(3) 579-597 (2002).
(Continued)

*Primary Examiner* — Brian J. Sines
(74) *Attorney, Agent, or Firm* — Edward J. Baba; Bozicevic, Field & Francis LLP

(57) ABSTRACT

Apparatus for testing the solubility of a medical dosage form includes a chamber (12) for holding a solvent medium (18), in the preferred embodiment a bicarbonate based buffer system. The apparatus also includes a pH probe (66) which is connectable to a supply of carbon dioxide (32, 34), as well as to a supply of helium (40), the supplies being controlled by a control unit (50). The control unit (50) monitors changes in pH of the solvent medium (18) and, as appropriate, feeds pH increasing and/or pH reducing gas from the supplies (32, 34, 40) into the chamber (12). The control unit (50) is able to maintain a uniform pH during testing or to provide a dynamically adjustable pH during testing, for example to three or more different pH levels in order to test the performance of a drug carrier at different levels of acidity or alkalinity for example, mimicking the conditions of the gastrointestinal tract. The apparatus (20) and associated method are particularly suitable for testing and developing dosage forms for oral delivery of drugs.

7 Claims, 3 Drawing Sheets

(51) Int. Cl.
　　　　*G01N 33/84*　　　(2006.01)
　　　　*G01N 33/15*　　　(2006.01)
　　　　*G01N 27/30*　　　(2006.01)

(58) Field of Classification Search
　　　USPC ..... 422/68.1, 62, 75, 81, 82.01; 436/43, 163
　　　See application file for complete search history.

(56) References Cited

U.S. PATENT DOCUMENTS

| | | |
|---|---|---|
| 5,807,115 A | 9/1998 | Hu |
| 7,331,251 B2 | 2/2008 | Das et al. |
| 7,723,119 B2 | 5/2010 | Stuart et al. |
| 9,222,927 B2 | 12/2015 | Hughes et al. |

OTHER PUBLICATIONS

Fadda et al. "Physiological Bicarbonate Buffers: Stabilisation and use as Dissolution Media for Modified Release Systems," International J. of Pharmaceutics 382(1-2) 56-60 (2009).

Heigoldt et al. "Predicting in vivo absorption behavior of oral modified release dosage forms containing pH-dependent poorly soluble drugs using a novel pH-adjusted biphasic in vitro dissolution test," European Journal of Pharmaceutics and Biopharmaceutics, 76(1) 105-111 (2010).

Lui et al. "Evolution of a physiological pH 6.8 bicarbonate buffer system: Application to the dissolution testing of enteric coated products," European Journal of Pharmaceutics and Biopharmaceutics, 78: 151-157 (2011).

APPARATUS AND METHOD FOR TESTING MEDICAMENTS

The present invention relates to apparatus and a method of testing the release characteristics of materials, particularly drugs, the release of which may be controlled by a second carrier material. The carrier material may be, for example, a coating which is designed for drug administration to the gastrointestinal tract and which is designed to release the coated drugs in response to changing pH.

The efficacy of many orally administered drugs is in many cases highly dependent upon their deposition at an appropriate location in the gastrointestinal tract. This may be due to factors such as inactivation (by for example release at an inappropriate pH or degradation by de-activating enzymes), uptake/solubility issues and so on. In other cases, the drug may be designed for administration locally at a particular region of the gut.

To address these issues, drugs may be packaged within coatings which are designed to release the therapeutic agent at the appropriate place and the prevalent means to achieve this is through the use of coatings formed from pH-sensitive polymers which are designed to dissolve at a specific pH. As the pH of a person varies along the person's digestive system, the theory is that a coating dissolvable at a particular pH will release the drug only when the coating is subjected to that pH and thus at the specific point in the digestive system. While the theory is sound and can lead to correct administration of the therapeutic agent, there are problems in the design and manufacture of such dosage forms or tablets, in particular in achieving the correct dissolution of the coating to match the desired gastrointestinal location.

More specifically, research into the efficacy of such coatings has revealed that in many cases these coatings are inconsistent in their drug-release characteristics in vivo, with failure rates higher than would be anticipated from in vitro analysis. The applicant has discovered that the currently employed in vitro dissolution testing undertaken in research and quality control of such pH-dependent formulations fails to provide an appropriate comparator to observations in vivo. Current methods utilise stirred tanks with buffering systems for which manipulation of the pH is simply achieved through the addition of acid or alkali. These ineffectively simulate the environment in vivo in that: 1) the characteristics of the buffers used differ significantly to physiological buffering and 2) the pH changes made (generally a rapid single switch from an acid environment to the appropriate pH) do not reflect the pH changes in the human gut.

The present invention seeks to provide an improved apparatus and method for testing medicaments and in particular the solubility of a coating or binding element of a dosage form, Further, the apparatus can be used for monitoring many other types of reaction which are pH-dependent, including monitoring of the dissolution of the drug itself. In principle, the applications of the invention may be extended to examination of the characteristics of any given substance—for example the relative activity of a drug, the characteristics of which may be modulated by changing pH, particularly insofar as this relates to the pH of the gastrointestinal tract.

According to an aspect of the present invention, there is provided apparatus for testing the solubility of a medical dosage form including: a chamber for holding a solvent medium and a dosage form for testing; a sensing device for sensing a parameter derivable from the chamber, the parameter being indicative of dissolution of a medical dosage form; a pH probe disposable in the chamber for measuring the pH of solvent medium in the chamber; a first valve coupling connectable to a supply of pH reducing fluid, the first valve coupling including a first conduit feeding into the chamber; a second valve coupling connectable to a supply of pH increasing fluid, the second valve coupling including a second conduit feeding into the chamber; and a control device connected to the probe and to the first and second valve couplings and operable to control the supply of pH increasing and pH reducing fluid into the chamber on the basis of the determined pH within the chamber.

The apparatus is able to provide a test environment in which a dosage form to be tested can be placed at or kept at the intended pH for testing, the pH being adjustable to ensure accurate replication of in vivo conditions.

Preferably, the apparatus includes a temperature sensor disposed to sense temperature in the chamber and coupled to the control device. The provision of a temperature sensor can ensure that the solution is kept at a temperature equivalent to the in vivo temperature, thus to ensure that the test is representative of actual dosage form usage. In the preferred embodiment, the apparatus may include a heating and/or cooling device for altering the temperature of the solvent and thus of the test environment.

In a practical embodiment, the sensing device includes a spectrometer.

Advantageously, the chamber includes an upper portion and a lower portion, and wherein at least one of the first and second conduits terminates at the upper portion of the chamber. In practice, this has the effect of pumping the pH changing fluid into the top of the solvent, which minimises movement or shaking of the solvent. Any such shaking will affect the disintegration rate of the dosage form or a coating thereof.

In an embodiment, the control device can be set to monitor a predetermined pH threshold and is operable to control the first and second valve couplings on the basis of the set threshold. Thus, the apparatus can be used to set different pH levels so as to test for different dosage forms or to test the performance of dosage forms under different physiological conditions. Advantageously, the control device is operable to control the first and second valve couplings so as to change the pH of solution in the chamber. Thus, the apparatus can test for disintegration of the dosage form in a particular pH window and lack of disintegration at other pH levels.

Preferably, the control device is operable to measure change in pH in the chamber during the supply of pH increasing and/or reducing fluid into the chamber. More specifically, the control device may be operable to determine change in pH on the basis of one or more of: rate of supply fluid, temperature and time. Advantageously, the control device is operable to control the supply of pH increasing and/or decreasing fluid on the basis of the determined change. Preferably, the control device is operable to determine said change in pH during a first control cycle and to control the supply of pH increasing and/or decreasing fluid in a subsequent cycle on the basis of the determined change during said first cycle. These features enable the construction of a system which is able to predict how the pH of the solution may change over time and thus maintain a more accurate and steady pH during testing. In one embodiment, the control device is operable to control the supply of pH increasing and/or decreasing fluid by controlling a time of supply, a rate of supply and/or an amount of supply.

In the preferred embodiment, the apparatus includes a plurality of chambers and a set of first and second valve couplings and conduits per chamber, wherein the control device is operable to control the supply of pH increasing and/or reducing fluid to each of the chambers.

There may be a single pH probe for the plurality of chambers, which provides a simple and cost effective device. In another embodiment, the apparatus includes a plurality of pH probes for the chambers, preferably a pH probe for each of the chambers.

Fluid supply into the chambers may be controllable in unison, in pluralities or individually.

The apparatus may be adapted to currently used instruments, for example those as referred to in the United States Pharmacopeia (USP) for testing dissolution of dosage forms. This includes for example, USP-I (rotating basket); USP-II (paddle); USP-III (reciprocating cylinder) and USP-IV (flow-through apparatus), however it is not limited to these or any other conformation.

The preferred embodiment provides a bicarbonate based media solution/buffer for the chamber or chambers. Bicarbonate based media are optimum for replicating the environment of the gastrointestinal tract and therefore in vivo conditions. However, as these media are unstable they have not generally been used in testing or have been used with mixed results. Previously published accounts of how such media may be stabilised by purging with carbon dioxide can be found in Liu F, Merchant H A, Kulkami R P, Alkademi M, Basit A W, 2011. Evolution of a physiological pH 6.8 bicarbonate buffer system: application to the dissolution testing of enteric coated products. Eur J Pharm Biopharm, 78(1):151-7; as well as in Fadda H M, Merchant H A, Arafat B T, Basit A W, 2009. Physiological bicarbonate buffers: stabilisation and use as dissolution media for modified release systems. Int J Pharm, 382(1-2):56-60.

The apparatus disclosed herein, however, allows both automated control over the otherwise unstable buffer pH (by provision of a self-correcting feedback mechanism) and automated switching of the buffer pH between pre-defined set points, allowing the instrument to mimic the changing pH found in the GI tract. It can also simulate the inter-individual variability in the gastrointestinal pH by using different pH set points in its chambers. In the preferred embodiment, the source of pH reducing fluid is a source of carbon dioxide, which may be pure carbon dioxide or a mixture of carbon dioxide and oxygen, (such as medical oxygen gas), Or may be a mixture of carbon dioxide and compressed air, or any suitable inert gas . . . . Carbon dioxide will stabilise the bicarbonate based medium which tends to lose carbon dioxide over time. Pure carbon dioxide will change pH levels rapidly, whereas use of a dilute mixture, such as a medical oxygen gas will replicate more accurately the natural process of carbon dioxide and bicarbonate buffer system in the gastrointestinal tract.

Advantageously, the source of pH-increasing fluid is helium. Helium counters rising carbon dioxide levels much more rapidly than is observed when allowing unaided escape. For slower pH change, an alternative pH-increasing fluid such as compressed air can be used.

According to another aspect of the present invention, there is provided a method of testing the solubility of a medical dosage form by means of apparatus which includes a chamber for holding a solvent medium and a dosage form for testing; a sensing device for sensing a parameter derivable from the chamber, the parameter being indicative of dissolution of a medical dosage form; a pH probe disposable in the chamber for measuring the pH of solvent medium in the chamber; a first valve coupling connectable to a supply of pH reducing fluid, the first valve coupling including a first conduit feeding into the chamber; a second valve coupling connectable to a supply of pH increasing fluid, the second valve coupling including a second conduit feeding into the chamber and a control device connected to the probe and to the first and second valve couplings and operable to control the supply of pH increasing and pH reducing fluid into the chamber on the basis of the determined pH within the chamber; the method including the steps of: providing in the chamber a solvent; providing in the chamber at least one dosage form to be tested; monitoring for the dissolution of the dosage form; and monitoring the pH of the solution and adjusting the pH of the solvent in the chamber by supplying one or both of the pH reducing and the pH increasing fluids.

In the preferred embodiment, the solvent is a bicarbonate based medium.

Advantageously, the method includes the step of supplying as the pH reducing fluid carbon dioxide, which may be pure carbon dioxide or a carbon dioxide and oxygen mixture such as about 95% oxygen and about 5% carbon dioxide or a mixture with compressed air or an inert gas. Preferably, the method includes the step of supplying as the pH increasing fluid helium or a compressed air.

Embodiments of the present invention are described below, by way of example only with reference to the accompanying drawings, in which.

It is to be understood that the apparatus and method disclosed herein can be used for testing any medicament in any form which is intended to be effective or released under particular pH conditions. The embodiments make reference to a dosage form, tablet or capsule, hereinafter referred collectively as a dosage form, which is intended to dissolve, disintegrate at a particular pH. This may be, for instance, by means of having the therapeutic agent of the dosage form held within a dissolvable coating or capsule, which coating or capsule dissolves at a particular pH. In other examples, the dosage form may include a therapeutic agent bound by a binding agent which dissolves, disintegrate at a particular pH. The nature of disintegration of the dosage form is not essential to the teachings herein. Similarly, the apparatus and method could be used for testing the efficacy of therapeutic or bioactive agents in any other dosage form.

The teachings herein are particularly useful in the testing and development of therapeutic agents which are intended to become effective at particular pH levels, such as within the gastrointestinal tract of a patient, where the pH of digestion fluids changes through the tract. The ability to administer a therapeutic agent at a particular point on the gastrointestinal tract (or gut) can be particularly advantageous. For instance, this makes it possible to administer drugs only at the location at which it is desired, with the result that the drug is more effectively administered, the drug does not reach zones not intended to be subjected to the drug, more potent doses of drug can be administered as the treatment can be localised, amongst other advantages.

Figure 1:
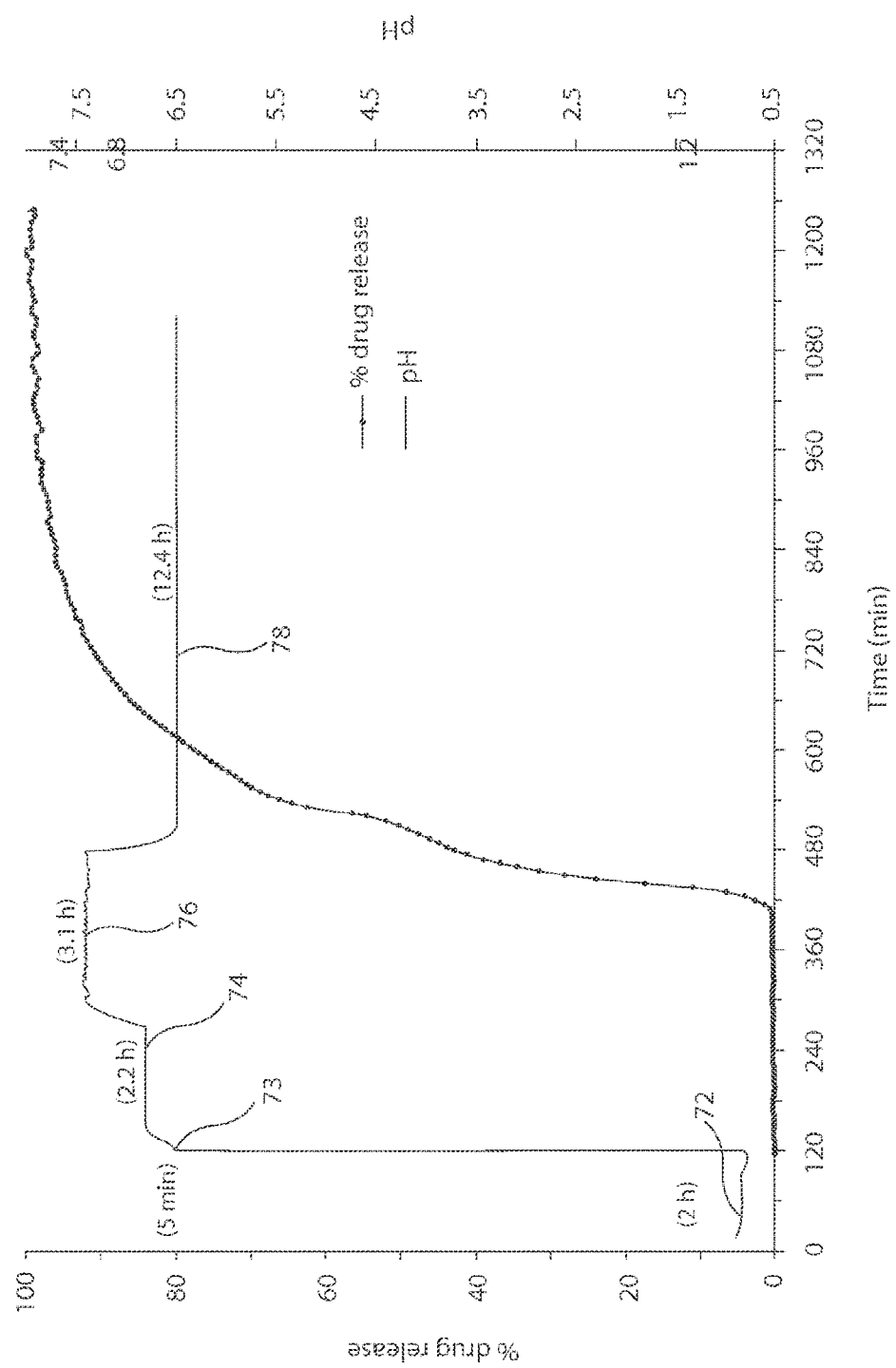
FIG. 1 is a graph of drug dissolution rate against pH of a solvent.

Referring now to FIG. 1, there is shown a graph of percentage drug release against pH for an example of dosage form. In this example, the dosage form has a therapeutic agent held within a capsule or coating which dissolves in a solvent at a particular pH. As can be seen in the graph, the dosage form is subjected to a varying pH over a period of around 20 hours or so. More specifically, the solvent has an initial pH of about 1 for a period 72 of 2 hours, the pH rapidly rising to around 6.5 for a period 5 minutes 73 and again to around 6.8 for a period 74 which lasts 2.2 hours. Thereafter, the pH is increased to around 7.5 for a period 76 of 3.1 hours thereafter dropping to a pH of around 6.5 of a subsequent period 78 of 12.4 hours. Of course, these times are indicated for illustration purposes only, as are the pH levels and can be adjusted according to the users requirements.

In this example, the coating of the dosage form is designed to dissolve only at a defined pH. Thus, for the first 7 hours or so of the routine, there is no noticeable release of drug from the dosage form as the coating remains intact. However, upon reaching the appropriate pH for dissolution of the dosage form, the coating gradually dissolves, leading to the release of the drug (therapeutic or bioactive agent) from within the dosage form. This can be seen in the graph of percentage increase in drug released, from a time after around 7 hours to around 12 hours or so from the start of the test, when substantially all of the drug has been released from the dosage form. This graph will reach a horizontal plateau once all the drug has been released.

The graph of FIG. 1 is in part theoretical in assuming that the pH of the solvent fluid can be maintained steady. This is the case for a number of solvents and reactions. However, in the case of the preferred solvent used in the taught apparatus and method, namely a bicarbonate based medium, the pH curve will generally not be level for the reason that bicarbonate based media cannot stably retain carbon dioxide, which has an effect of the pH of the media. It is for this reason that known test apparatus and methods tend to avoid the use of bicarbonate based media. With regard to the pH curve of FIG. 1, an unstable medium would fail to maintain a constant pH during a test and thus to problems with measuring the efficacy of a drug coating or binding agent. By contrast, the apparatus and method taught herein are able to maintain a bicarbonate based medium substantially stable during the test period, as shown in FIG. 1.

The stabilisation mechanisms taught herein constantly adjust the balance of carbon dioxide in the bicarbonate based medium, thereby to maintain a substantially uniform pH of the solvent solution for the period when it is desired that this be uniform. It will be appreciated that in practical circumstances, a generally uniform pH is maintained subject to system hysteresis. Of course, the apparatus and method taught herein, whilst optimising the use of a bicarbonate based medium as a solvent, can be used with many other types of solvent, including solvents which are not unstable in terms of their pH.

FIG. 1 also shows that with proper design and manufacture of coatings and binding agents, for example, it is possible to design for drug release at very specific pH levels, thereby enabling the administration of the drug at specific locations within a patient. Moreover, the test taught herein is able to measure the performance of the release agent, that is coating, binding agent or other element, when subjected to a variety of different solvent pH levels, as would be the case when the drug is administered through a patient's gastrointestinal tract.

The dosage form, could be designed for general use but may also be designed for a specific patient, for example for localised treatment of a specific gastrointestinal problem, such as inflammatory bowel disease, for cancer treatment and so on in which the pH profile may be quite different to the healthy gut. Individuals vary widely in terms of the pH recorded in transit through the gut and in the time taken for transit. In this regard, it is thus envisaged that a probe, of known type, could be inserted into a patient to measure the specific pH levels through that patient's gastrointestinal tract. In this way, the pH of the patient's gastrointestinal tract can be accurately measured and a dosage form specifically designed for delivery of a therapeutic agent at the desired location only. Such a dosage form can be tested in-vitro by using the apparatus and methods taught herein, simulating the conditions in gastrointestinal tract.

The specific embodiments described below provide a real-time drug dissolution and monitoring instrument. The instrument allows the use of physiologically-relevant buffers in which the pH is controlled by bubbling gas into a test chamber. pH is monitored in real time and used to regulate automatically gas flow so as to stabilise and alter the reaction pH. The system can thereby be controlled to mimic accurately changing pH in the gastrointestinal tract over time.

The apparatus and method taught herein are thus unique in that following in vivo monitoring of the pH of individual test subjects (through ingestion of a pH recording device), this data can be used to replicate accurately the pH changes recorded. Thus, correlation between the in-vitro and in-vivo performance of drug formulation can be made and a specific dosage form/coating manufactured, incorporating the inter-individual variability in the gastrointestinal pH of a population.

The preferred embodiment of apparatus is shown with reference to FIGS. 2 and 3 below.

Figure 2:
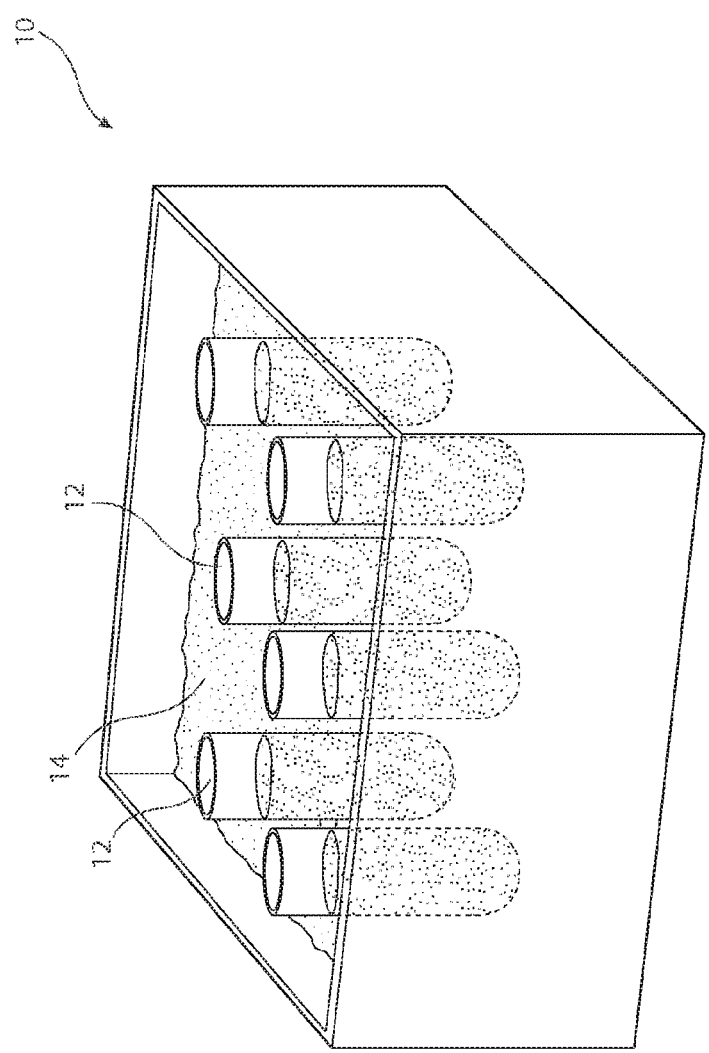
FIG. 2 is a schematic diagram of an example of test chamber assembly.
Figure 3:
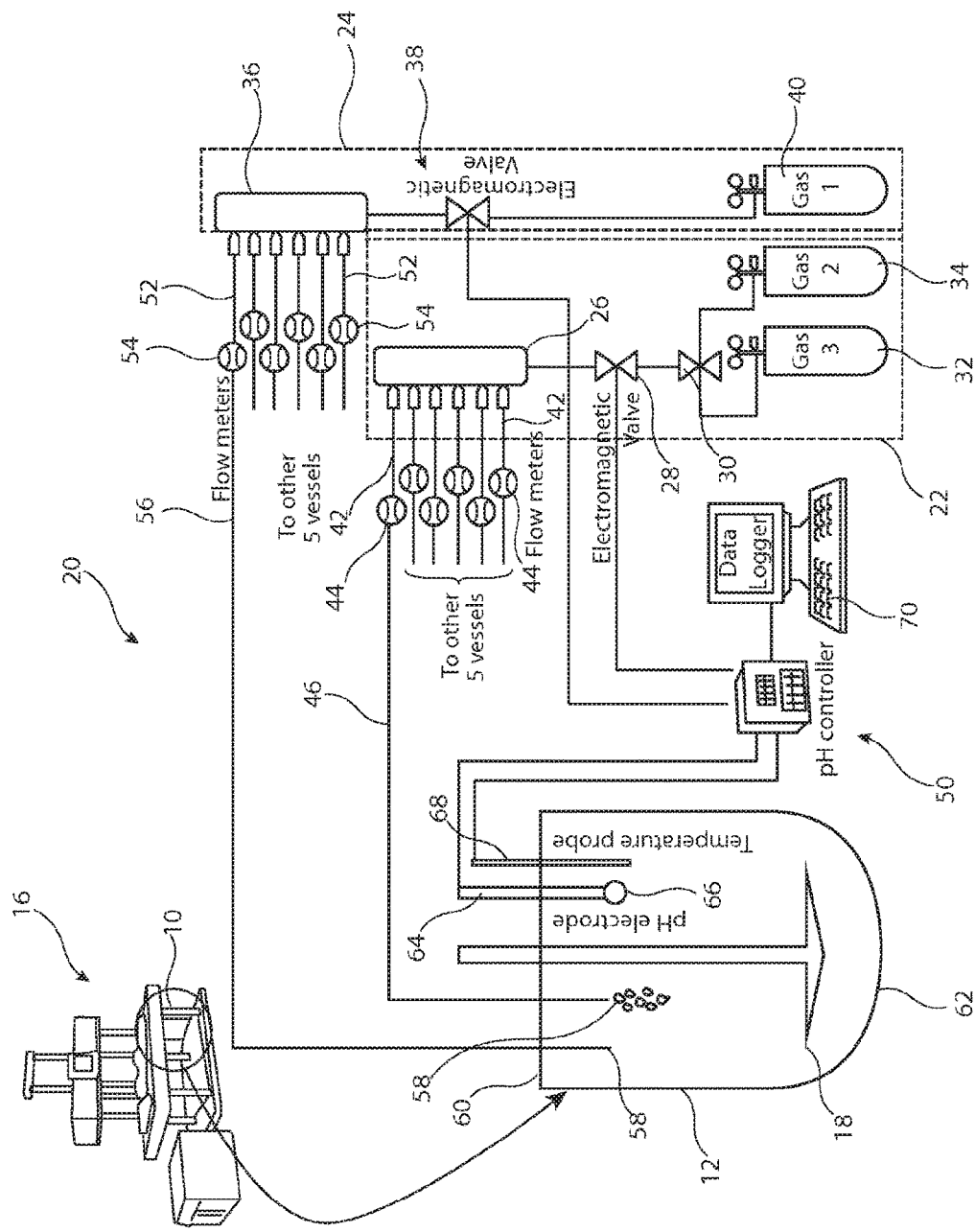
FIG. 3 is a schematic diagram of an embodiment of the apparatus.

Referring first to FIG. 2, there is shown in schematic form an example of test chamber bath 10 for use with the apparatus shown in detail in FIG. 3. More specifically, in the example described, there are provided six test chambers 12 for testing six different dosage forms, or other medicament carriers, under similar conditions. The bath 10 is filled with a stabilising liquid 14, which may be distilled/deionised water. The test chambers 12 are held within the bath 10 so as to be substantially immersed in the stabilising liquid 14, thereby ensuring that the six test chambers 12 are kept at substantially uniform temperature, alternatively the vessels can also be heated by other suitable means, for example climatic chamber or jacketed vessels. This arrangement of bath and test chambers is known in the art and therefore is not described in further detail herein.

Referring now to FIG. 3, there is shown partly in schematic form a preferred embodiment of test apparatus in accordance with the teachings herein. The bath 10 and test chambers 12 are held within test device 16 which provides for appropriate heating and cooling of the stabilisation liquid 14, as well as monitoring of the general operation of the test apparatus, including monitoring for reactions within the test chambers 12. In this regard, the apparatus 16 may also include in this example a spectrometer or a chromatographic system for monitoring the optical changes in the solution with the test chambers 12 in order to monitor reactions therewithin or can be attached to an auto-sampler for further analysis. The spectrometer can be used to determine the amount of drug released, by changes in colour or other optical properties of the solution within the test chambers 12 during the reaction. This is a procedure which is known in the art and therefore is not be described in detail herein. The skilled person will appreciate that other monitoring methods may be used including, for example, monitoring for conductivity, heat changes, effervescence and so on.

The other components shown in FIG. 3 are the principal elements of the test apparatus taught herein and which can usefully be incorporated within the components of the device 16 which are used to control the state of the bath 10 and to monitor the reactions within the test chambers 12. It is envisaged also that the apparatus taught herein could be provided as a separate unit which in coupled to or bolted on the device 16, thereby to be able to used or fitted as after sales item.

Specifically, the apparatus 20 includes a first unit 22 which, as explained below, provides for the supply of pH reducing fluid to the solvent 18 within the test chambers 12, and a second unit 24 for the supply of pH increasing fluid into the solvent 18. The unit 22 includes a coupling 26 which in this example is a manifold assembly able to feed fluid to each of the six test chambers 12 within the bath 10. The unit 22 also includes a first valve 28, which in this example is an electromagnetic valve. The valve 28 is coupled to a second valve 30, which may also be an electromagnetic valve or a manually operated valve, which couples to first and second gas supplies, in this example gas cylinders. The gas supply 32 is in this embodiment is a mixture of oxygen and carbon dioxide, typically medical oxygen gas having preferably about 95% oxygen and about 5% carbon dioxide. The supply 34, on the other hand, is in the preferred embodiment pure carbon dioxide.

The provision of two different pH reducing fluids provides the possibility of reducing pH of the solvent 18 in the test chamber 12 at different rates, with pure carbon dioxide providing a much higher rate of reduction in pH than the oxygen/carbon dioxide mix, which can be used for fine tuning the pH level. In this regard, the valve 30 could be a manually operable valve which enables manual selection between the gas supplies 32 and 34, for instance at the start of a test or during a test while changing the pH set points to a level where low doses of carbon dioxide may be needed. In other embodiments, the valve 30 could be coupled to control unit 50, described in further detail below, so as to be operated automatically in dependence upon control signals provided by the control unit 50.

It is to be appreciated that in some embodiments there may be provided only a single supply of pH reducing gas, for instance pure carbon dioxide or a carbon dioxide/oxygen mix. In such as case, the valve 30 would not be necessary. However, the provision of valve 30 may provide an additional option to the operator if the need arises.

The second unit 24 includes a manifold assembly 36 of similar structure to the manifold 26 and designed to couple supply of pH increasing fluid into the six test chambers 12. The manifold assembly 36 is coupled to an electromagnetic valve 38, this being preferably the same type as the electromagnetic valve 28. The valve 38 is coupled to a gas supply 40, which provides a pH increasing gas, in this example helium.

In the preferred embodiment, the solvent 18 is a bicarbonate based medium such as physiological salt solutions predominantly buffered by bicarbonate species, simulating the pH, buffer capacity and ionic composition of the gastrointestinal fluids. Examples of such buffers are provided in Liu and Fadda referred to above, although an appropriately skilled person will be capable of designing other buffering systems which can be modulated using the techniques and instrumentation disclosed herein. Such media can replicate accurately the fluids in the gastrointestinal tract. However, as explained above, bicarbonate based media are unstable in terms of their pH. The reason is that bicarbonate based media are unable to retain carbon dioxide, the loss of which causes a rise in pH of the media. The supply unit 22 is able to replenish carbon dioxide in the solvent 18, thereby to maintain its pH stable. The use of a control unit 50 can achieve this automatically and in a manner which can mitigate the disadvantages of such media. On the other hand, the supply unit 24, which in this example feeds helium into the solvent, has the effect of degassing the solvent 18, in particular by forcing carbon dioxide to be expelled from the medium 18. Loss of carbon dioxide raises the pH of the solvent 18. It will be appreciated that were time available, the unit 24 could be omitted and the release of carbon dioxide from the solvent medium 18 allowed to occur naturally with a consequential natural increase in the pH of the solvent medium. However, this can result in much slower response times of the system and in particular slower than occur in vivo. In the preferred embodiment, therefore, the supply 24 is provided so as to enable rapid increases in pH of the solvent medium 18 and to enable the replication of real time in vivo conditions in the gut.

Referring again to the unit 22, the manifold assembly 26 includes six exit ports 42 each coupled to a respective flow meter 44 for measuring flow fluid from the manifold assembly into respective conduits 46 leading to associated test chambers 12. The flow meters 44 provide a measure of the amount of pH reducing fluid which is fed to the individual test chambers 12. The flow meters 44 may be coupled, via the controller 50, to valves (not shown) within the manifold assembly 26 so as to control the amount, in particular rate, of fluid which is fed into the conduits 46. In a simpler embodiment, there may be provided valves in the manifold which are adjusted solely during calibration of the apparatus, typically to ensure that there is the same flow rate into each conduit 46.

The manifold assembly 36 is likewise provided with six outlets 52 which are coupled via flow meters to respective conduits 56 which themselves lead to associated test chambers 12. The flow meters 53 are likewise coupled, for instance via the control unit 50, to valves within the manifold assembly 36 so as to control the amount (rate) of pH increasing fluid into the test chambers 12, or to manually adjustable calibration valves.

The conduits 46 and 56, which are typically relatively small tubes, feed into respective test chambers 12. As can be seen in FIG. 3, in the preferred embodiment, the conduits 46 and 56 terminate in the chambers 12 at positions 58 close to the top 60 of the chambers 12 and remote from the base 62 thereof. In an embodiment, the conduits 46, 56 terminate at positions 58 which are in the region of or preferably less than 10% of the total depth from the top 60 to the bottom 62 of the chambers 12. In a practical embodiment, the position 58 is no more than around 2 centimeters from the liquid surface, this of course being dependent upon the dimensions of the chambers. As a result, fluid from the supplies 32, 34 and/or is fed towards to the top of the solvent medium 18 rather than at the bottom as may otherwise have been considered as the logical input position. The advantage of this is that any fluids supplied into the solvent medium 18 do not create turbulence within the medium 18. It has been found that such turbulence can alter the conditions/hydrodynamics within the medium 18 and in particular may accelerate any reaction, thereby to failing to replicate the in vivo conditions.

As mentioned above, the apparatus 20 also includes a control unit 50 for controlling the pH of the solvent medium 18 in the test chambers. The control unit 50 is coupled to at least one pH sensor 64 having a probe or electrode 66 located within a chamber 12, at a depth sufficient to be located within the solvent medium 18. There is also provided, in the preferred embodiment, a temperature probe 68 coupled to the control unit 50 for monitoring the temperature of the solvent medium 18. The temperature probe 68 is optional as simpler systems can rely upon the temperature of the stabilising liquid 14 of the bath 10 to give an indication of the temperature of the solvent medium 18. Of course, it is preferred that a temperature probe 68 used so as to measure the actual temperature of the fluid medium as this may not be the same as that of the bath liquid 40.

In the preferred embodiment, there is provided a pH electrode 66 for each of the six test chambers 12. There may also be a temperature probe 68 for each of the test chambers 12, thereby to provide for individual monitoring and control of the test environments in each of the test chambers 12. However, simpler embodiments may provide pH electrodes 66 (and as appropriate temperature probes 68) in only some of the test chambers 12, with the simplest embodiment having only a single pH electrode 66 in one of the test chambers 12. In this latter embodiment, a measure taken of one of the chambers 12 is assumed to be indicative of the states of all of the chambers 12 of the group. With uniform supply of pH reducing and/or increasing fluid into the chambers 12 and the same solvent medium and other test conditions, a single measure of pH and, as desired temperature, within the chambers 12 is likely to be sufficient.

The control unit 50 is thus able to monitor the pH level of the solvent medium 18 in the chambers 12 and from that determination to control the operation of the electromagnetic valves 28, 38 (and where provided 30) in order to control the supply of pH reducing and pH increasing fluid into the chambers 12, thereby to control the pH of the solvent medium 18. In addition, the control unit 50 is, when provided with one or more temperature probes 68, able to monitor the temperature of the solvent medium 18 and determine either whether the temperature is satisfactory for the test to be representative of in vivo conditions or to control the heating and/or cooling of the solvent medium 18 in the chambers 12, 10o typically by heating or cooling the bath fluid 14 by means of suitable heating or cooling elements (not shown).

The apparatus may also include a data logger 70, which may be a computer or other similar device, able to keep a log of data obtained during operation of the apparatus. Control unit 50 and data logger 70 could be part of the same device.

The provision of six chambers 12 enables, for example, up to six identical tests to be carried out simultaneously under the same conditions in order to ensure reliability of the tests, as is conventional in the field. On the other hand, the apparatus 20 is, in the preferred embodiment at least, sufficiently sophisticated to be able to control and monitor different reactions in each of the six test chambers 12, for instance reactions at different pH levels, tests on different medicaments, tests at different temperatures and so on. This can, for example, assist in the development of different dosage form structures, be it coatings, binding agents or any other pH-dependent reagent.

As explained above, the preferred embodiment uses a bicarbonate based medium as the solvent medium 18 such as disclosed in references Liu and Fadda referred to above as well as carbon dioxide to reduce pH and helium to increase pH. These are considered ideal fluids for testing dosage forms as well as the efficacy of therapeutic agents under different pH conditions of the gastrointestinal tract.

The apparatus 20 operates, in the preferred embodiment, in the following manner. Prior to commencement of a test, the solvent medium 18 in the chambers 12 is brought to the desired operating conditions of temperature and pH. Temperature is preferably body temperature in order to replicate conditions within the gastrointestinal tract. In practice, the temperature of the solvent medium 18 is kept at around 37° C. (body temperature). Control of temperature, both initially and during the test, is important, not only to replicate in vivo conditions but also because pH of the solvent medium 18 can change with temperature.

The system 20 also initially balances the pH of the solvent medium 18 on the basis of a measure of pH from the pH electrode 66 and control of the electromagnetic valves 28 and 38 as appropriate. Once the desired stable pH and temperature are attained in the chambers 12, a dosage form, in this example, is introduced into each of the chambers 12. Where fewer than six dosage forms or other medicine carriers are to be tested, only some of the chambers 12 are used. At the same time, or before insertion of the dosage form into the chambers 12, the monitoring device (for example spectrometer), is operated so as to monitor the state of the solvent medium 18 and thus of any reaction within the chambers 12.

When it is desired to test the performance of a dosage form or other drug carrier within the gastrointestinal tract, it is preferred that the pH of the solvent medium 18 is adjusted over a period equivalent to the time taken for passage of a dosage form through the gastrointestinal tract and at different pH levels experienced throughout the gastrointestinal tract. An indication of these pH levels and time of passage can be obtained from a patient ingestible pH probe of known type, the data from which can be configured into the control unit 50 and, where provided, data logger 70. An example of pH levels set and maintained in the chambers 12 is given in FIG. 1, explained above.

More specifically, referring to FIG. 1 again, the pH levels identified as 72 to 78 are intended to be indicative of the pH of digestive fluids within the gastrointestinal tract of a patient at different points along the tract and during the digestion process. In this example, it is desired to provide a medicament at the end of the intestine and thus at the end of the digestive process, in which case the dosage form or other medical carrier is designed to release the therapeutic agent only at pH levels which occur at that portion of the digestion. Thus, using the example of FIG. 1 for description, the control unit 50 controls the pH of the solvent medium 18 in the chambers 12 from an initial low pH of around 1 in period 72, to a pH of around 6.8 in period 74, rising to a pH of around 7.4 for period 76 and then dropping to a pH of around 6.5 for period 78. Other set-points can be set dependent upon the desired conditions. During the entirety of the periods 72 to 78, the system monitors for drug release by virtue of measurements obtained by the spectrometer. When it is necessary to raise the pH level in the solvent medium 18, for example from period 72 to period 74 in FIG. 1, the control unit 50 operates the electromagnetic valve 38 to pump helium from the source 40 through the manifold assembly 36 into the chambers 12 by their respective conduits 56. The feeding of helium into the solvent medium 18 degasses the system, forcing the release of carbon dioxide, thereby raising the pH of the medium 18. During this process, the control unit 50 continuously monitors the pH of the medium 18 until the next desired set point, in this example 6.8, at which juncture the control unit 50 closes the electromagnetic valve 38 and thereafter operates the electromagnetic valves 28, 38 selectively, in order to maintain a constant pH during the period 74. A similar control operation occurs between periods 74 and 76, whereas from period 76 to 78, the control unit 50 operates the electromagnetic valve 28 to supply either pure carbon dioxide or a carbon dioxide mixture through the manifold assembly 26 via the conduits 46 into the chambers 12 so as to inject carbon dioxide into the solvent medium 18 to reduce its pH until the new desired point of 6.5. Once that level has been reached, the control unit 50 operates the electromagnetic valves 28 and 38 in what could be termed a steady state in order to maintain the pH of the solvent medium 18 steady during the period 78.

Of course, the control unit 50 can be programmed to control the pH of the solvent medium 18 in a chamber 12 as desired for the particular test, be it better to replicate in vivo conditions or any other test conditions which are desired for a particular test routine, such as quality control tests in pharmaceutical manufacturing. Similarly, in an embodiment, the control unit 50 can adjust the temperature of the solvent medium 18 either to take into account temperature changes caused by the reaction (in this example release of the medicament and dissolution of the coating or binding agent), as well as to replicate changes in temperature which might occur in vivo. Edwards et al., has demonstrated, for example, that temperature at different regions within the healthy human gut is variable, dependent upon, for example, changes occurring during the natural circadian rhythm (see Edwards B, Waterhouse J, Reilly T, Atkinson G, 2002: "A comparison of the suitabilities of rectal, gut, and insulated axilla temperatures for measurement of the circadian rhythm of core temperature in field studies"; Chronobiol Int., 19(3): 579-97).

The control unit 50 can thus provide a completely automated test environment which not only can replicate accurately and in real time in vivo conditions but which can also stabilise a bicarbonate based medium, thus enabling testing with bicarbonate buffers so as to mimic in vivo conditions. Use of a spectrometer or other measuring device can provide real time analysis of the performance of a dosage form or other drug carrier. In addition, by supplying the pH reducing and/or increasing fluids to the top of the chambers 12, bubbling or turbulence of the solvent medium 18 is minimised, which might otherwise accelerate the reaction and thus fail to provide an accurate replica of in vivo conditions.

It will be appreciated that as well as providing dynamic changes in pH over time in order to replicate in vivo conditions, the control unit 50 could be operated to maintain a constant pH for the entire period of a test, as desired for any particular test routine, such as quality control tests in pharmaceutical manufacturing. It is envisaged also that the control unit 50 and apparatus 20 could be set up to control the chambers 12 differently from one another so as to effect different test routines.

It is preferred that the control unit 50 is provided with logic/algorithms to effect what could be described as intelligent dosing of the solvent medium 18 to maintain a very uniform pH of the solvent medium 18 particularly during a test period. More specifically, in combination with the data logger 17, in one embodiment to the control unit 50 remembers the effect of administering to the solvent medium 18 pH reducing and/or pH increasing fluid, in particular the amount of fluid which was administered, the change in pH following the administration and optionally the rate of change in pH. The control unit 50 can also be programmed or arranged to record changes in pH of solvent medium 18 occurring naturally over time or as a result of the reactants within the chamber 12. The advantage of recording and using such data is that the control unit 50 can adapt the processes for administering pH reducing and/or pH increasing fluids even before the pH of the solvent medium 18 moves beyond a set threshold, in what could be described as a predictive control operation. A reactive control mode is also available as an option, which waits until the pH of the solvent medium 18 exceeds or drops below a predetermined threshold may be insufficiently rapid to maintain uniform pH of the solvent medium 18 in the chamber 12.

In contrast, and as in the preferred embodiment, the control unit 50, by storing this data, is able to analyse the effect of a previous dose of pH reducing and/or increasing fluid on the pH of the solvent medium 18 in the chamber 12, to determine whether that dose was sufficient to provide a required change in pH and if deemed insufficient, to increase the dose in a subsequent cycle. Similarly, if the previous dose was too great, the control system can reduce the dose in a subsequent cycle. The dose of fluid can be altered by adjustment of the flow of fluid through the manifold assembly 26, 36, through the individual conduits 46, 56 and/or by the length time of during which fluid is administered. Similarly, the control unit 50 can be operated to begin administering a dose of pH changing fluid before a threshold is reached, in order to take into account lag in changes in pH.

Changing the dosage in this manner, the skilled person will appreciate, can be used to calibrate the control unit 50 in particular the administration of pH changing fluids to provide as uniform a pH in the chamber 12 as possible. This calibration can also be used to take into account changes caused by using different solvent media 18, to take into account different reactions, as well as different reactive conditions.

In place of, or in addition to, the flow meters 44, 54, there may be provided pressure controllers operable to control the pressure of fluid passing through the conduits 46, 56 and thereby the dosage of such fluid.

In the case where not all of the chambers 12 are provided with a pH electrode and/or temperature probe, it is preferred that dummy electrode/probes having the same physical forms/shapes are located in those chambers without such probes/electrodes, in order to replicate the fluid dynamic conditions within all of the chambers 12.

Although the preferred embodiments described above make reference to use of gases to adjust the pH level of the solvent medium 18, it is to be appreciated that pH changing liquids may also be used.

The system taught herein provides dynamic and in the preferred embodiment real time control of the pH of the solvent medium for the purpose of testing dosage forms and other drug carriers and has the ability to replicate in real time in vivo conditions. It is possible to use as a solvent medium a bicarbonate buffer which more closely replicates digestive fluids within a patient. Therefore, the system can provide much more reliable testing of dosage forms and other drug carriers, both for testing the efficacy of devices as well as for use in the design and development of dosage forms and other drug carriers.

It is to be understood that although in the preferred embodiment the chambers are disposed in a temperature regulation bath they may be heated by any other suitable means, such as but not limited to, jacketed vessel or a climatic chamber.

The invention claimed is:

1. A method of testing the solubility and/or dissolution of a medical dosage form by means of apparatus which includes a chamber for holding a solvent medium and a dosage form for testing; a sensing device for sensing a parameter derivable from the chamber, the parameter being indicative of dissolution of a medical dosage form; a pH probe disposable in the chamber for measuring the pH of solvent medium in the chamber; a first valve coupling connectable to a supply of pH reducing fluid, the first valve coupling including a first conduit feeding into the chamber; a second valve coupling connectable to a supply of pH increasing fluid, the second valve coupling including a second conduit feeding into the chamber; and a control device connected to the probe and to the first and second valve couplings and operable to control the supply of pH increasing and pH reducing fluid into the chamber on the basis of the determined pH within the chamber; the method including the steps of:
- providing in the chamber a solvent, the solvent being a bicarbonate based medium;
- providing in the chamber at least one dosage form to be tested;
- monitoring for the dissolution of the dosage form; and
- monitoring the pH of the solution and adjusting the pH of the solvent in the chamber by supplying one or both of the pH reducing and the pH increasing fluids.

2. The method according to claim 1, including the step of supplying as the pH reducing fluid carbon dioxide.

3. The method according to claim 2, wherein one of the following is supplied:
- pure carbon dioxide;
- a carbon dioxide and oxygen mixture; and
- a mixture of about 95% oxygen and about 5% carbon dioxide.

4. The method according to claim 1, including the step of supplying as the pH increasing fluid one of:
- helium;
- compressed air, and
- a inert gas.

5. The method according to claim 1 including the steps of monitoring a predetermined pH threshold and controlling the first and second valve coupling on the basis of the set threshold so as to change the pH of the solution in the chamber.

6. The method according to claim 1, wherein the medical dosage form comprises a pH-dependent carrier material capable of controlling the release of a drug or other substance.

7. The method according to claim 1, wherein the pH-dependent change is release of a drug or other substance by disintegration of the medical dosage form.

* * * * *